United States Patent
Bowers

(10) Patent No.: US 7,094,433 B1
(45) Date of Patent: Aug. 22, 2006

(54) COMPOSITION FOR DOMESTIC LIVESTOCK GRAFTING AND METHOD OF MAKING AND USING

(76) Inventor: Kent A. Bowers, 207 Lakeside La., Pierre, SD (US) 57501-5212

( * ) Notice: Subject to any disclaimer, the term of this patent is extended or adjusted under 35 U.S.C. 154(b) by 0 days.

(21) Appl. No.: 11/133,936

(22) Filed: May 20, 2005

Related U.S. Application Data

(62) Division of application No. 10/206,307, filed on Jul. 26, 2002, now abandoned.

(51) Int. Cl.
*A61K 36/534* (2006.01)
*A01N 65/00* (2006.01)

(52) U.S. Cl. .................................................... 424/747
(58) Field of Classification Search ................. 424/747
See application file for complete search history.

(56) References Cited

U.S. PATENT DOCUMENTS

| | | | | |
|---|---|---|---|---|
| 4,495,033 A | * | 1/1985 | Rathbun et al. ............. | 202/118 |
| 5,487,898 A | * | 1/1996 | Lu et al. ...................... | 424/435 |
| 5,891,501 A | * | 4/1999 | McKellip et al. ............ | 426/489 |
| 6,139,795 A | * | 10/2000 | Gaillard et al. ................ | 422/5 |
| 6,800,294 B1 | * | 10/2004 | Ryan et al. .................. | 424/405 |
| 2002/0110576 A1 | * | 8/2002 | Messina ...................... | 424/411 |

OTHER PUBLICATIONS http'.//-.herbdatanz.com/aromatherapy-and-the essential oils—8.htm which is a reproduction Extra Pharmacopoeia,☐☐Martindale, Twenty-fourth Edition 1958.*

* cited by examiner

*Primary Examiner*—Herbert J. Lilling

(57) ABSTRACT

A composition for domestic livestock grafting for application to a prospective mother and a juvenile animal to be cared for by the prospective mother to mask the natural scents of the prospective mother and the juvenile animal to induce acceptance of the juvenile animal by the prospective mother includes a mint oil or mixture of mint oils, water, and an emulsifier, preferably utilizing peppermint oil and polysorbate 80 as the emulsifier. Methods of making and using the composition are also disclosed.

14 Claims, No Drawings

COMPOSITION FOR DOMESTIC LIVESTOCK GRAFTING AND METHOD OF MAKING AND USING

REFERENCE TO RELATED APPLICATION

This application is a divisional of application Ser. No. 10/206,307, filed Jul. 26, 2002 now abandoned.

BACKGROUND OF THE INVENTION

1. Field of the Invention

This invention relates to domestic livestock grafting, specifically to a new composition using peppermint oil to aid in the mothering acceptance of domestic livestock such as cows, horses, sheep, and goats.

2. Description of the Prior Art

The grafting of domestic livestock has been a problem throughout the history of ranching and farming. Whenever a mother rejects a baby, whether it is biologically hers or an orphaned young animal, grafting (attempting to overcome that rejection to unite a baby animal with a mother animal) becomes necessary. There are two main instances when domestic grafting becomes a necessity. Using cows as an example, the first instance is when a mother rejects its biological baby. It is a common occurrence for a new heifer to reject it own calf, especially when the heifer has not given birth to a calf before. Typically, this is due to inexperience and lack of mothering instinct. The second instance where grafting becomes a necessity is in cases in which a mother cow has lost its biological baby and an orphaned calf is given to her in place of the lost calf. The mother cow often does not accept the orphaned calf because it is not biologically hers. She will often reject it and even harm the calf in attempts to keep it from feeding. Up to this point there has been no remedy that works consistently. The commercial products are sporadically effective and generally inconvenient in their application.

Scent and taste have a great deal to do with the grafting of livestock. A mother cow often may reject the scent and/or taste of her own calf if it differs from her own scent. Likewise, a foster mother will often reject an orphaned calf because it does not carry her scent.

Some products have attempted to remedy this problem by camouflaging the scent and/or the taste of the calf through various means. These products typically include disadvantages including but not limited to the following.

At least one commercially available product warns of potential contamination of food and water with which it comes in contact. This becomes an inconvenience and danger when you consider that the instructions recommend that you restrain the animals in an enclosed facility such as a barn. In such a facility one would be surrounded by hay, feed, and water that could be contaminated and would probably be consumed by livestock. Also once a foster mother has adopted a calf, she often licks the calf. Use of a potential contaminant may be quite harmful for the mother to directly lick it off of the newly adopted calf.

Currently commercially available products can have a very undesirable odor. Some products attempt to hide the calf's scent with ammonia. The odor is very offensive and can give a burning sensation to ones nostrils from the fumes.

Commercially available products may contain animal by-products as its first and main ingredient. There are many potential side affects that can accompany the consumption of animal by-products. The use of them is becoming more and more undesirable.

Application of currently available products can be inconvenient. If the calf is not wet or damp, the applicator needs access to water or syrup. The applicator must dampen the calf to help a powdery substance adhere to the animal. It is sometimes recommended that syrup be poured over the calves back to secure adhesion of the powder. The need to add an additional ingredient, whether water or syrup, is less convenient than a product that doesn't require the presence of such a substance.

Currently available commercial products are not safe products for children to handle. These products post label warnings to keep the substance out of the reach of children.

Finally, the success rate of currently available commercial products is less than the success rate of the present invention.

SUMMARY OF THE INVENTION

Accordingly, there are many advantages of my livestock grafting formula. Several objects and advantages of the present invention are:

(a) to provide an effective aid in the mothering acceptance of livestock grafting. When tested on cows, my composition was over 97% effective within 24 hours.

(b) to provide a formula that consistently quickens the grafting process to a 24-hour time frame.

(c) to provide a completely safe livestock-grafting formula through the use of all-natural mint oil.

(d) to provide a formula for livestock grafting that is safe for the environment and humans.

(e) to provide a formula that is easy to apply to livestock.

(f) to provide a formula that does not require the presence of a second substance to make it work effectively, thus making it more convenient to apply.

(g) to provide a formula that is appealing in smell for both humans and livestock.

(h) to provide a formula that is desirable to taste for all livestock.

(i) to provide a formula that can be used effectively on all domestic livestock including cows, horses, sheep, and goats.

To meet the above objectives, the present invention is a livestock-grafting aid containing peppermint oil, water, and an emulsifier, preferably polysorbate 80, for external application to domestic livestock to aid in the mothering acceptance process.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty that characterize the invention, are pointed out with particularity in the claims annexed to and forming a part of this disclosure.

DESCRIPTION OF THE PREFERRED EMBODIMENT

A new composition for domestic livestock grafting embodying the principles and concepts of the present invention generally comprises a liquid having three main ingredients: a mint oil, water, and an emulsifier. The mint oil is diluted with water. Then the emulsifier is added to form an emulsion.

The emulsifier may be selected from propylene glycol, polysorbate 60, polysorbate 20, polysorbate 80, and polyoxyethyene glycol. Polysorbate 80 is preferred because a small amount is required to form the desired emulsion compared to the other listed emulsifiers.

The preferred method of composing the livestock-grafting aid is to combine the following ingredients in an enclosed glass container.

| Ingredients | Amount by ounces |
|---|---|
| mint oil | .5 |
| polysorbate 80 | .25 |
| purified water | 2 |

Once the above ingredients are combined, heat the container in a high-powered microwave having at least 700 Watts of power on high setting (or the like) for 45 seconds. Allow the container to cool slightly then add 14 ounces of room temperature purified water. For purposes of this disclosure, room temperature may be broadly defined as between 60 and 100 degrees Fahrenheit and more specifically as between approximately 65 and 75 degrees Fahrenheit. Re-cover the container and shake the container vigorously. The final mint oil mixture, which comprises the formula of the invention, is represented by the following formulation:

| Ingredients | Amount by ounces |
|---|---|
| mint oil | .5 |
| polysorbate 80 | .25 |
| water | 16 |
| Total: | 16.75 ounces |

After the formula is completed, it is placed in a plastic squirt bottle for easy application.

Operation of Invention

The mint oil is the active ingredient in the grafting formula. Peppermint oil is an essential oil obtained by distilling peppermint, also called mentha piperata, from the dried leaves and flowering tops of mentha piperata. Mentha arvensis, a mint produced in India and commonly used as a peppermint substitute in foreign countries, may be used with nearly equal results as mint oil prepared from mentha piperata. Subsequent description will use the term peppermint oil which is intended to broadly describe the oil prepared from either mentha piperata or mentha arvensis. Other kinds of mint oil can be used, although they have been found to be less effective. Scotch spearmint (mentha cardiaca) and native spearmint (mentha spicata) both work to some degree. The peppermint oil has an extremely strong scent and taste and therefore is the preferred mint oil to use. The peppermint oil acts as a camouflaging agent that disguises both the scent and taste of the rejected/orphaned animal.

While the above mixture utilizing a substantially pure single mint oil is found best for use with cattle, a mixture of 75% peppermint oil and 25% spearmint oil is preferred for use with sheep because spearmint oil cuts through the natural oils present on the wool better than peppermint oil. Thus, a combination of spearmint oil and peppermint oil enhances the ability of the mixture to stick to the wool with minimal loss of the strong scent and taste of the peppermint oil.

The potent mint oil is diluted with the water. Pure mint oil is expensive and extremely potent in nature. Water is a perfect all-natural and safe ingredient to use to dilute the peppermint oil.

The polysorbate 80 acts as the emulsifier between the water and peppermint oil. Polysorbate 80 is a completely safe composition that is also found in commercially available substances like some brands of flavored gelatin, mouthwash, lotion, and cosmetics.

While there is no desire to be bound by a theory that polysorbate 80 causes livestock acceptance, its presence in the grafting formula does enhance the convenience of the invention. Without the emulsifier, the composition would have to be shaken between each squirt. There would also be a greater chance of uneven application of the active ingredient, peppermint oil, on the animal. The presence of the polysorbate 80 completely takes care of these concerns without altering the effectiveness or harmlessness of the grafting solution.

Further and for clarification here and in the claims, use of the term "prospective mother" is intended to define both an adoptive mother being grafted to a juvenile born to another animal and a natural birth mother of a juvenile animal that has previously rejected the juvenile animal.

The preferred directions for applying the grafting solution are as follows:

1. Restrain the mother in a "squeeze chute" or something similar for the safety of the person applying the solution.
2. Cover the mother's eyes and generously apply solution directly to her nose and mouth. The natural menthol contained in the peppermint oil can sting the animal's eyes, although it is not actually harmful to the animal. Due to the pleasant taste of the mint oil the mother cow will begin to lick her mouth and face. The scent is also strong causing her to only be able to smell the aroma of the mint solution.
3. Cover the orphan/rejected calf's eyes and generously apply to nose, head and back. Applying the solution to the baby is a vital part of the adoption process. The mother cow will not be able to smell the calf's true scent; rather she can only recognize the appealing scent of the mint solution, which is also scenting her body. She will then begin to lick the calf because the calf tastes good to her. The peppermint grafting solution camouflages the scent and taste of the calf and in essence convinces the mother that the calf belongs to her because it smells and tastes the same as she does.
4. After application to mother and baby, allow the baby to nurse the mother while she is still being restrained.
5. One application will generally work, but the process will occasionally need to be repeated 12 hours later.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of facilitating acceptance of a juvenile animal by a prospective mother, the steps of the method comprising:

forming a grafting solution for application to said prospective mother and said juvenile animal, said grafting solution including a mint oil;
applying said grafting solution to said prospective mother;
applying said grafting solution to said juvenile animal;
uniting said prospective mother and said juvenile animal to permit contact between said prospective mother and said juvenile animal.

2. The method of claim 1, wherein said step of applying said grafting solution to said prospective mother further comprises:
applying said grafting solution to an area of said prospective mother surrounding nasal and oral cavities of said prospective mother to mask said prospective mother's ability to sense a natural scent of said prospective mother.

3. The method of claim 1, wherein said step of applying said grafting solution so said juvenile animal further comprises:
applying said grafting solution to said juvenile animal's nose, head and back.

4. The method of claim 1, the steps of the method further comprising:
restraining said prospective mother prior to applying said grafting solution.

5. The method of claim 2, the steps of the method further comprising:
covering eyes of said prospective mother during application of said grafting solution to said prospective mother.

6. The method of claim 3, the steps of the method further comprising:
covering eyes of said juvenile animal during application of said grafting solution to said juvenile animal.

7. A method of making a livestock grafting solution for application to a prospective mother and a juvenile animal to be cared for by the prospective mother to mask the natural scents of the prospective mother and the juvenile animal to induce acceptance of the juvenile animal by the prospective mother, the steps of the method comprising:
mixing water and a mint oil to form a solution.

8. The method of claim 7, the steps of the method further comprising:
mixing an emulsifier into said solution to form an emulsified solution.

9. The method of claim 7, the steps of the method further comprising:
heating said emulsified solution; and
adding additional water to said emulsified solution to form a final solution.

10. The method of claim 8 wherein said water is between 69% and 76% by volume of a total volume of said emulsified solution, said emulsifier is between 7% and 11% of said total volume of said emulsified solution, and said mint oil is between 14% and 22% of said total volume of said emulsified solution.

11. The method of claim 8 wherein said water is 2/2.75 of a total volume of said emulsified solution, said emulsifier is 0.25/2.75 of said total volume of said emulsified solution, and said mint oil is 0.5/2.75 of said total volume of said emulsified solution.

12. The method of claim 9 wherein said water and said additional water combined is between 95% and 96% by volume of a total volume of said final solution, said emulsifier is between 1% and 2% by volume of said total volume of said final solution, and said mint oil is between 2% and 4% by volume of said total volume of said final solution.

13. The method of claim 9 wherein said water and said additional water combined is 16/16.75 by volume of a total volume of said final solution, said emulsifier is 0.25/16.75 by volume of said total volume of said final solution, and said mint oil is 0.5/16.75 by volume of said total volume of said final solution.

14. The method of claim 9 wherein said heated emulsified solution is allowed to cool for a pre-determined period of time prior to mixing said additional water with said emulsified solution; and
wherein said additional water is at a temperature between 60 and 100 degrees Fahrenheit when said additional water is mixed with said emulsified solution.

* * * * *